(12) United States Patent
Lee et al.

(10) Patent No.: US 12,390,216 B2
(45) Date of Patent: Aug. 19, 2025

(54) MEDICAL THREAD HAVING POLYGONAL CROSS-SECTIONED STOPPER ON ONE END, AND MANUFACTURING METHOD FOR SAME

(71) Applicant: SAMYANG HOLDINGS CORPORATION, Seoul (KR)

(72) Inventors: Ho Sung Lee, Daejeon (KR); Dae Hui Ryu, Daejeon (KR); Hye Sung Yoon, Yongin-si (KR)

(73) Assignee: SAMYANG HOLDINGS CORPORATION, Seoul (KR)

( * ) Notice: Subject to any disclaimer, the term of this patent is extended or adjusted under 35 U.S.C. 154(b) by 219 days.

(21) Appl. No.: 17/923,388

(22) PCT Filed: Mar. 24, 2021

(86) PCT No.: PCT/KR2021/003623
§ 371 (c)(1),
(2) Date: Nov. 4, 2022

(87) PCT Pub. No.: WO2021/241868
PCT Pub. Date: Dec. 2, 2021

(65) Prior Publication Data
US 2023/0190266 A1  Jun. 22, 2023

(30) Foreign Application Priority Data
May 27, 2020 (KR) .................. 10-2020-0063530

(51) Int. Cl.
*A61B 17/06* (2006.01)
*A61B 17/00* (2006.01)
(Continued)

(52) U.S. Cl.
CPC ........ *A61B 17/06166* (2013.01); *A61L 17/10* (2013.01); *B29C 51/30* (2013.01);
(Continued)

(58) Field of Classification Search
CPC .......... A61B 17/06166; A61B 17/0401; A61B 2017/00526; A61B 2017/06176; A61L 7/10
See application file for complete search history.

(56) References Cited

U.S. PATENT DOCUMENTS

2010/0294105 A1* 11/2010 Genova ............ A61B 17/06166
83/879
2013/0103078 A1  4/2013 Longo et al.
(Continued)

FOREIGN PATENT DOCUMENTS

EP       3714802 A1   9/2020
JP       2002-702 A   1/2002
(Continued)

OTHER PUBLICATIONS

International Search Report, issued in PCT/KR2021/003623, PCT/ISA/210, dated Jul. 1, 2021.
(Continued)

*Primary Examiner* — Tan-Uyen T Ho
*Assistant Examiner* — Cherie M Poland
(74) *Attorney, Agent, or Firm* — Birch, Stewart, Kolasch & Birch, LLP (57) ABSTRACT

The present invention relates to a medical thread which has on one end thereof a stopper that has a polygonal cross-section, and which exhibits excellent end adhesive force and penetration resistance, and to a manufacturing method for same.

13 Claims, 2 Drawing Sheets

(51) Int. Cl.
  *A61L 17/10*    (2006.01)
  *B29C 51/30*    (2006.01)
(52) U.S. Cl.
  CPC ............... *A61B 2017/00526* (2013.01); *A61B 2017/06176* (2013.01)

(56) References Cited

U.S. PATENT DOCUMENTS

| | | | |
|---|---|---|---|
| 2013/0238021 A1* | 9/2013 | Gross | D02J 3/02 606/228 |
| 2016/0045636 A1 | 2/2016 | Rizk et al. | |
| 2016/0106411 A1* | 4/2016 | Rousseau | G06F 16/148 156/169 |
| 2016/0106422 A1* | 4/2016 | Lindh, Sr. | A61B 17/0401 606/228 |
| 2019/0046184 A1 | 2/2019 | Jung | |

FOREIGN PATENT DOCUMENTS

| | | |
|---|---|---|
| JP | 2019-503826 A | 2/2019 |
| KR | 10-1855328 B1 | 5/2018 |
| KR | 10-2018-0134483 A | 12/2018 |
| KR | 10-2019-0139010 A | 12/2019 |
| KR | 10-2053392 B1 | 12/2019 |
| KR | 10-2020-0000114 A | 1/2020 |

OTHER PUBLICATIONS

Extended European Search Report for European Application No. 21812763.7, dated Apr. 19, 2024.

\* cited by examiner

MEDICAL THREAD HAVING POLYGONAL CROSS-SECTIONED STOPPER ON ONE END, AND MANUFACTURING METHOD FOR SAME

TECHNICAL FIELD

The present invention relates to a medical thread having a stopper with polygonal cross section at one end and exhibiting excellent stopper attachment force and penetration resistance, and a method for manufacturing the same.

BACKGROUND ART

In general, medical threads are used for various purposes including sealing or suturing damaged parts of tissues, such as skin, muscles, tendons, internal organs, bone tissues, nerves, blood vessels and the like, as well as for closing and binding together tissues in surgical incisions during surgical interventions, for repair, support and/or fixation of bodily tissues.

When using conventional medical threads in order to stitch incised tissues, formation of a knot is required. However, there are various knotting methods and since some of them are quite complicated, application of conventional medical threads demands preliminary training. Another problem is that knotting consumes a considerable share in the total duration of the surgical procedure. Accordingly, a need to develop a medical thread that can be used without forming a knot has emerged.

To address the need for knotless thread a barbed thread has been developed (for instance, Korean Patent Laid-open Publication No. 10-2019-0061944). Barbed thread can be classified into a bidirectional type having barbs formed in both directions and a unidirectional type having barbs formed in one direction only. Since the former bidirectional type has barbs facing in opposite directions, suturing starts from the center of the wound and continues in both directions to the end of the incision, bi-directional barbed threads obviate the need to secure the end of the thread with the knot. The latter unidirectional type, however, has barbs resisting movement, when in tissue, in the direction only that is opposite from the direction in which the barbs face, therefore a means for fixing the medical thread at the end of the incision is necessary.

In order to fix the end of such a unidirectional type barbed thread, the anchoring effect is achieved by processing the end part in a loop shape, stitching the tissue with suture needle and approaching the loop close to the tissue, one more stitching and passing the suture needle through the loop, and tightening the thread. Prior art is the passing a thread through a small loop molded at the end of the unidirectional type barbed thread with the consequent tightening of the loop to achieve the anchoring effect. A solution of reducing complexity and inconvenience of the procedure and reducing time required to fix the end of the unidirectional barbed thread is demanded.

CONTENTS OF THE INVENTION

Problems to be Solved

The present invention is to resolve the problem of prior art as stated above. Accordingly, the purpose of the present invention is to provide a medical thread capable of fixing the end of the medical thread to skin tissue in a short time and exhibiting excellent stopper attachment force and penetration resistance at the same time, and a method for manufacturing the same.

Technical Means

An aspect of the present invention provides a medical thread comprising: a body; and a stopper connected to one end of the body, wherein the end of the body connected to the stopper has a circular cross section, wherein the body is extended along the longitudinal direction, wherein the stopper has a polygonal cross section at the part connected to the body, and wherein two or more of the distances from the center of gravity of the polygonal cross section of the stopper to each vertex of the stopper are larger than the radius of the circular cross section of the end of the body.

In an embodiment, the two or more of the distances from the center of gravity of the polygonal cross section of the stopper to each vertex of the stopper can be 1.5 times or more of the radius of the circular cross section of the end of the body.

In an embodiment, the stopper can be placed perpendicularly to the longitudinal direction of the body adjacent thereto, and have a shape of polygonal prism or polygonal pyramid.

Also, in an embodiment, the stopper can have a thickness of 0.1 mm to 5 mm.

Also, in an embodiment, a side of the polygonal cross section of the stopper at the part connected to the body can have a length of 1 mm to 5 mm.

Also, in an embodiment, the edge of the stopper can be formed in a tapered shape.

Also, in an embodiment, the attachment force between the body and the stopper (stopper attachment force) can be 2 kgf or higher.

Also, in an embodiment, the penetration resistance of the stopper can be 0.15 kgf or higher.

Also, in an embodiment, the materials of the body and the stopper can be the same or different from each other, and each of the body and the stopper independently can comprise one or more polymers selected from polydioxanone (PDO), polycaprolactone (PCL), polylactic acid (PLA), polyglycolic acid (PGA), polytrimethylcarbonate (PTMC), polypropylene (PP), Nylon and polytetrafluoroethylene (PTFE), and copolymers thereof.

Also, in an embodiment, the medical thread can have a surgical needle combined to the other end of the body which is not the end connected to the stopper.

Also, in an embodiment, the surface of the body can comprise plural barbs protruding outward (or projecting from the body).

Another aspect of the present invention provides a method for manufacturing a medical thread, comprising the steps of: preparing a body extended along the longitudinal direction; heating and melting one end of the body; injecting the melted end of the body into a mold having a predetermined shape to form a stopper at the end of the body; cooling and separating the body and the stopper from the mold, wherein the end of the body connected to the stopper has a circular cross section, wherein the stopper has a polygonal cross section at the part connected to the body, and wherein two or more of the distances from the center of gravity of the polygonal cross section of the stopper to each vertex of the stopper are larger than the radius of the circular cross section of the end of the body.

In an embodiment, the method for manufacturing a medical thread can further comprise step of adjusting the position of the stopper relative to the melted end of the body.

Also, in an embodiment, in the step of cooling and separating the body and the stopper from the mold, the body and the stopper can be cooled with a cooling air amount of 0.01 to 3 mpa for a time of 5 to 120 seconds.

Also, in an embodiment, in the step of heating and melting one end of the body, the heating temperature can be 50 to 400° C.

Effect of the Invention

The medical thread according to the present invention exhibits better stopper attachment force and penetration resistance as compared with a thread having a circular stopper of the same area of cross section, and thus by using it, the end can be fixed more firmly to the skin tissue.

CONCRETE MODE FOR CARRYING OUT THE INVENTION

The present invention is explained in detail below.

The medical thread of the present invention comprises a body; and a stopper connected to one end of the body, wherein the end of the body connected to the stopper has a circular cross section, wherein the body is extended along the longitudinal direction, wherein the stopper has a polygonal cross section at the part connected to the body, and wherein two or more—more concretely, three or more—of the distances from the center of gravity of the polygonal cross section of the stopper to each vertex of the stopper are larger than the radius of the circular cross section of the end of the body.

In an embodiment, the two or more of the distances from the center of gravity of the polygonal cross section of the stopper to each vertex of the stopper can be 1.5 times or more—more concretely, 2 times or more, 2.5 times or more, 3 times or more, 3.5 times or more, 4 times or more, 4.5 times or more, or 5 times or more—of the radius of the circular cross section of the end of the body. In addition, the two or more of the distances from the center of gravity of the polygonal cross section of the stopper to each vertex of the stopper can be 15 times or less—more concretely, 14.5 times or less, 14 times or less, 13.5 times or less, 13 times or less, 12.5 times or less, or 12 times or less—of the radius of the circular cross section of the end of the body.

More concretely, the two or more (preferably, three or more) of the distances from the center of gravity of the polygonal cross section of the stopper to each vertex of the stopper can be 1.5 times to 15 times—still more concretely 2 times to 15 times, still more concretely 5 times to 15 times, and still more concretely 5 times to 12 times—of the radius of the circular cross section of the end of the body.

In an embodiment, the stopper can be placed perpendicularly to the longitudinal direction of the body adjacent thereto, and have a shape of polygonal prism or polygonal pyramid.

In an embodiment, without limitation thereto, the polygon of the cross section of the stopper can be, for example, triangle as the simplest, square, pentagon or hexagon, or it may a polygon of various shape such as star shape, cross shape, or the like. In addition, the stopper can have a shape of polygonal prism or polygonal pyramid corresponding to such a polygonal cross section.

In an embodiment, the stopper can have a thickness of 0.1 mm to 5 mm, and more concretely 0.1 mm to 3 mm or 0.1 mm to 1 mm. If the stopper is too thinner than the above, such stopper may not stop at the skin tissue and thus it may break away therefrom. If the stopper is too thicker than the above, such stopper may cause pain due to feeling of foreign body.

In an embodiment, a side of the polygonal cross section of the stopper at the part connected to the body can have a length of 1 mm to 5 mm, more concretely 1 mm to 4 mm or 2 mm to 4 mm, and still more concretely 1 mm to 3 mm or 2 mm to 3 mm.

In an embodiment, the attachment force between the body and the stopper (stopper attachment force) can be 2 kgf or higher, and more concretely 2.1 kgf or higher, 2.2 kgf or higher, 2.3 kgf or higher, 2.4 kgf or higher, or 2.5 kgf or higher. There is no special limitation to the upper limit of the stopper attachment force, and it can be, for example, 10 kgf or lower, 9 kgf or lower, 8 kgf or lower, or 7 kgf or lower, but it is not limited thereto.

In an embodiment, the penetration resistance of the stopper can be 0.15 kgf or higher, and more concretely 0.16 kgf or higher, 0.17 kgf or higher, 0.18 kgf or higher, 0.19 kgf or higher, or 0.2 kgf or higher. There is no special limitation to the upper limit of the penetration resistance of the stopper, and it can be, for example, 1 kgf or lower, 0.9 kgf or lower, 0.8 kgf or lower, 0.7 kgf or lower, 0.6 kgf or lower, or 0.5 kgf or lower, but it is not limited thereto.

In an embodiment, in case of using a yarn of 30 Size standard according to Pharmacopedia of the United States of America (USP) as the body of the medical thread, the stopper attachment force can be 2.5 kgf or higher and the penetration resistance can be 0.2 kgf or higher—which are the better properties as compared with a thread having a yarn of the same standard and a circular stopper of the same surface area of cross section.

In an embodiment, in case of using a yarn of 00 Size standard according to USP as the body of the medical thread, the stopper attachment force can be 4.5 kgf or higher and the penetration resistance can be 0.4 kgf or higher—which are the better properties as compared with a thread having a yarn of the same standard and a circular stopper of the same surface area of cross section.

In an embodiment, in case of using a yarn of 01 Size standard according to USP as the body of the medical thread, the stopper attachment force can be 5.2 kgf or higher and the penetration resistance can be 0.3 kgf or higher—which are the better properties as compared with a thread having a yarn of the same standard and a circular stopper of the same surface area of cross section.

In an embodiment, in case of using a yarn of 02 Size standard according to USP as the body of the medical thread, the stopper attachment force can be 5.2 kgf or higher and the penetration resistance can be 0.3 kgf or higher—which are the better properties as compared with a thread having a yarn of the same standard and a circular stopper of the same surface area of cross section.

In an embodiment, the body and the stopper can be formed from the same material or from different materials, and each of them independently can comprise one or more polymers selected from polydioxanone (PDO), polycaprolactone (PCL), polylactic acid (PLA), polyglycolic acid (PGA), polytrimethylcarbonate (PTMC), polypropylene (PP), Nylon and polytetrafluoroethylene (PTFE), and copolymers thereof. Herein, polydioxanone (PDO), polycaprolactone (PCL), polylactic acid (PLA), polyglycolic acid (PGA) and polytrimethylcarbonate (PTMC) are bio-absorbable polymer materials, and polypropylene (PP), Nylon and polytetrafluoroethylene (PTFE) are non-absorbable polymer materials.

In an embodiment, the body and the stopper can be formed from the same material. For example, after forming the body first, the stopper can be formed from the same material by melting the material of the body.

In an embodiment, the medical thread can have a surgical needle combined to the other end of the body which is not the end connected to the stopper.

Any kind of surgical needle can be used without limitation to its type as long as it can be inserted into the skin tissue and can penetrate the skin tissue.

In an embodiment, when the surgical needle is combined to the other end of the body which is not the end connected to the stopper of the medical thread, the two or more (preferably, three or more) of the distances from the center of gravity of the polygonal cross section of the stopper to each vertex of the stopper can be 1.5 times or more—more concretely 2 times or more, still more concretely 2.5 times or more—of the radius of the outer diameter of the surgical needle (i.e., the circular cross section of the needle). In addition, the two or more of the distances from the center of gravity of the polygonal cross section of the stopper to each vertex of the stopper can be 7 times or less—more concretely 6 times or less, still more concretely 5 times or less—of the radius of the outer diameter of the surgical needle.

More concretely, the two or more (preferably, three or more) of the distances from the center of gravity of the polygonal cross section of the stopper to each vertex of the stopper can be 1.5 times to 7 times—still more concretely 2 times to 6 times, and still more concretely 2.5 times to 5.5 times—of the radius of the outer diameter of the surgical needle.

In an embodiment, the surface of the body can comprise plural barbs protruding outward (or projecting from the body).

The body can be formed in a thin and long shape extended along the longitudinal direction, and can have flexible property so that it may be deformed by external force. Herein, the longitudinal direction can be understood as a direction of extending of the center axis of the body.

In the outer side of the body, plural barbs tangentially (or obliquely) inclined in the longitudinal direction can be provided, and the plural barbs can be formed on the surface of the body with a predetermined angle to the longitudinal direction of the body. For example, the plural barbs can be angulated to the longitudinal direction of the body at 10° to 45° angles. By forming the plural barbs having a predetermined angle on the surface of the body as such, the plural barbs can be easily entangled to the skin tissue. The plural barbs herein can be formed along one direction (unidirectional type). Thus, according to an embodiment, the medical thread of the present invention can be a unidirectional type barbed thread.

Concretely, a first barb can be formed on the surface of one side of the body, and a second barb and a third barb can be formed on the surface of the other side of the body, spaced in circumferential direction from the first barb. And, the first barb, the second barb and the third barb can be formed in plurality, and each of them can be aligned (or arranged) in a row along the longitudinal direction of the body. Also, the first barb, the second barb and the third barb can be formed to have different angles relative to one other.

The medical thread according to the present invention can be a thread for use in suturing the part of the tissue wounded owing to surgical intervention or external injury, or a thread inserted into skin tissue and used for skin tightening.

In an embodiment, the edge of the stopper can be formed in a tapered shape, and in this case, the pressure applied to skin tissue by the edge of the stopper can be dispersed, consequently resulting in reduction of pain for the patient.

Also, the stopper can be placed perpendicularly to the longitudinal direction of the body. That is, the cross section of the stopper can be perpendicular to the body, and thus the medical thread can be easily entangled to the skin tissue.

Also, the center of the stopper can meet the longitudinal center of the body. In this case, the body can be placed at the center of the stopper, and thus the medical thread can be entangled to the skin tissue in balance.

Also, the above-explained barbs formed on the body in a unilateral direction can resist the one-directional movement of the medical thread, and in addition, the stopper provided at the end of the body can resist the counter-directional movement of the medical thread. That is, the medical thread can be fixed in the tissue of the subject by the barbs and the stopper.

Another aspect of the present invention provides a method for manufacturing a medical thread, comprising the steps of: preparing a body extended along the longitudinal direction; heating and melting one end of the body; injecting the melted end of the body into a mold having a predetermined shape to form a stopper at the end of the body; cooling and separating the body and the stopper from the mold, wherein the end of the body connected to the stopper has a circular cross section, wherein the stopper has a polygonal cross section at the part connected to the body, and wherein two or more of the distances from the center of gravity of the polygonal cross section of the stopper to each vertex of the stopper are larger than the radius of the circular cross section of the end of the body.

According to an embodiment, the body is prepared first, and one end of the body is heated and melted. Concretely, to melt the end of the body, the body is placed in a transfer unit that can transfer the body, and the body is injected into a pre-heated mold so that the end of the body can be heated and melted.

According to an embodiment, the step of preparing the body can further comprise a step of forming plural barbs on the surface of the body.

In an embodiment, the rate for injecting the body into the mold by the transfer unit can be 0.1 to 2 mm/s. Herein, if the injection rate is less than 0.1 mm/s, the productivity can decline, and if it is greater than 2 mm/s, the injection of the body might be performed faster than its melting and thereby the body might bend or injection itself might fail. Preferably, the rate for injecting the body into the mold by the transfer unit can be 0.1 to 1 mm/s, or 0.1 to 0.7 mm/s.

Figure 4:
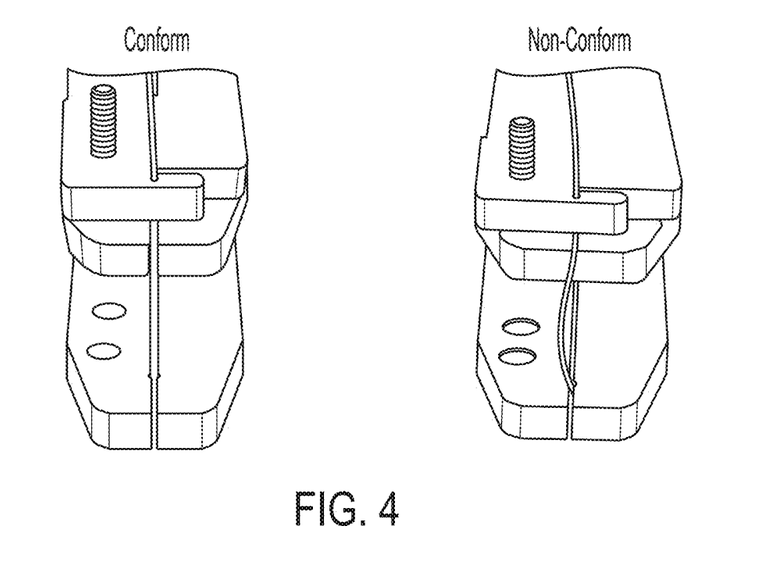
FIG. 4 is an example of the standard for determining "Conform (not bent)"/"Non-Conform (bent)" according to whether the body is bent or not while injecting the body into a mold by diameter size and injection rate.

In an embodiment, the suitable injection rates according to the raw material and size of the body were confirmed, and the relationship therebetween is represented in the following Table 1. As shown in FIG. 4, the body was injected into the mold at an injection rate adjusted within the range of from 0.4 mm/s to 1.1 mm/s according to the diameter size of the body, and how much the body was bent was observed by naked eye, and if the yarn was bent, it was determined as "Non-Conform," and if the body was not bent, it was determined as "Conform." The diameter size of the body means the diameter size of the yarn which was not barbed.

In an embodiment, in the cooling step, the cooling air amount can be 0.01 to 4.5 mpa, 0.01 to 4 mpa, 0.01 to 3.5 mpa, 0.01 to 3 mpa, 0.01 to 2 mpa, 0.01 to 1 mpa, 0.01 to 0.5 mpa, 0.01 to 0.3 mpa, or 0.01 to 0.2 mpa. If the cooling air amount is less than 0.01 mpa, the cooling may be insufficient and thereby the molded product might not be discharged, and if the cooling air amount is greater than 4.5 mpa, the cooling might become excessive, which might result in reduction of attachment force between the body and the stopper.

More concretely, the cooling air amount can be 0.01 mpa or more, 0.02 mpa or more, 0.03 mpa or more, 0.04 mpa or more, 0.05 mpa or more, 0.06 mpa or more, 0.07 mpa or more, 0.08 mpa or more, or 0.09 mpa or more, and 4.5 mpa or less, 4.0 mpa or less, 3.5 mpa or less, 3.0 mpa or less, 2.5

TABLE 1

| Material of the body | Diameter of the body (USP Size or EP Size) | Injection rate (mm/s) | | | | | | | |
|---|---|---|---|---|---|---|---|---|---|
| | | 0.4 | 0.5 | 0.6 | 0.7 | 0.8 | 0.9 | 1.0 | 1.1 |
| PDO | 02 | Conform | Conform | Conform | Conform | Conform | Conform | Conform | Non-Conform |
| | 01 | Conform | Conform | Conform | Conform | Conform | Conform | Conform | Non-Conform |
| | 00 | Conform | Conform | Conform | Conform | Conform | Conform | Conform | Non-Conform |
| | 20 | Conform | Conform | Conform | Conform | Conform | Conform | Conform | Non-Conform |
| | 30 | Conform | Conform | Conform | Conform | Conform | Conform | Conform | Non-Conform |
| PGCL | 01 | Conform | Conform | Conform | Conform | Non-Conform | Non-Conform | Non-Conform | Non-Conform |
| | 00 | Conform | Conform | Conform | Conform | Non-Conform | Non-Conform | Non-Conform | Non-Conform |
| | 20 | Conform | Conform | Conform | Conform | Non-Conform | Non-Conform | Non-Conform | Non-Conform |
| | 30 | Conform | Conform | Conform | Conform | Non-Conform | Non-Conform | Non-Conform | Non-Conform |

PDO: polydioxanone;
PGCL: poly(glycolide-co-caprolactone)

According to an embodiment of the present invention, the mold can be heated by a heating unit, and the heating temperature can be 50 to 400° C. If the heating temperature is lower than 50° C., the body is not melted, and if it is higher than 400° C., excessive melting of the body in the mold may impede cooling, or lead to scorching and sticking of the body onto the mold. Preferably, the heating temperature can be 150 to 250° C.

Thereafter, the melted end of the body is injected into the mold having a predetermined shape so that the stopper can be formed at the end of the body.

In an embodiment, the mold having a predetermined shape can be of a shape of polygonal prism or polygonal pyramid as explained above.

Then, after the step of adjusting the position of the stopper relative to the end of the body, the stopper can be formed so that its center is positioned at the center of the body.

In an embodiment, the adjustment of the relative position between the stopper and the body can be carried out by adjusting the position of the transfer unit for the body or the position of the mold.

Then, after the step of cooling and separating the body and the stopper from the mold, the medical thread wherein the stopper is formed at one end of the body can be manufactured.

mpa or less, 2.0 mpa or less, 1.5 mpa or less, 1.0 mpa or less, 0.5 mpa or less, 0.4 mpa or less, 0.3 mpa or less, 0.2 mpa or less, or 0.1 mpa or less.

In an embodiment, in the cooling step, the cooling time can be 5 to 120 seconds, and more concretely, it can be 5 to 100 seconds, 5 to 80 seconds, 5 to 60 seconds, 5 to 50 seconds, 10 to 100 seconds, 15 to 80 seconds, 20 to 60 seconds, 25 to 50 seconds, 30 to 50 seconds, 25 to 45 seconds, 30 to 45 seconds, or 35 to 45 seconds. If the cooling time is less than 5 seconds, inappropriate shape may be formed, and if it is greater than 120 seconds, the production speed may decrease. According to an embodiment of the present invention, the cooling air amount can be 0.1 mpa or less, and the cooling time can be 35 to 45 seconds.

Meanwhile, the rate for injecting the body into the mold to form the stopper can vary depending on the size of the mold and the material of the body.

In an embodiment, the appearance and attachment force of the stopper depending on the cooling time were measured during manufacturing of the stopper under the fixed conditions of: 0.8 mm/s for PDO and 0.6 mm/s for PGCL with the injection rate of the body varying according to the size; 0.5 mpa as the cooling air amount; and 5 seconds as the waiting time after completion of the injection. The results are represented in the following Table 2. The stopper attachment force was evaluated as Excellent/Non-Conform according to the criteria shown in the following Table 3. That is, if the measured stopper attachment force was higher than the permit criteria of Table 3, it was determined as "Excellent," and if the measured value was lower than the criteria, it was determined as "Non-Conform." The diameter of the body means the diameter of the yarn which was not barbed.

TABLE 2

| Material of the body | Diameter of the body (USP Size or EP Size) | Cooling time (s) | | |
|---|---|---|---|---|
| | | 5 | 15 | 20 |
| PDO | 02 | Non-Conform | Excellent | Excellent |
| | 01 | Non-Conform | Excellent | Excellent |
| | 00 | Non-Conform | Excellent | Excellent |
| | 20 | Non-Conform | Excellent | Excellent |
| | 30 | Non-Conform | Excellent | Excellent |

| Material of the body | Diameter of the body (USP Size or EP Size) | Cooling time (s) | | |
|---|---|---|---|---|
| | | 30 | 35 | 40 |
| PGCL | 01 | Excellent | Excellent | Excellent |
| | 00 | Excellent | Excellent | Excellent |
| | 20 | Excellent | Excellent | Excellent |
| | 30 | Excellent | Excellent | Excellent |

TABLE 3

| Size | Acceptance criteria Average stopper attachment force (kgf) |
|---|---|
| 02 | 1.80 |
| 01 | 1.80 |
| 00 | 1.50 |
| 20 | 1.10 |
| 30 | 0.68 |

The present invention is explained in more detail through the following Examples and Comparative Examples. However, the scope of the present invention is not limited to the Examples.

EXAMPLES

The yarns used in Examples and Comparative Examples below are represented in the following Table 4.

TABLE 4

| | Material | USP Size or EP Size | Initial strength |
|---|---|---|---|
| Example 1/Comparative Example 1 | PDO | 02 | Conform |
| Example 2/Comparative Example 2 | PDO | 00 | Conform |
| Example 3/Comparative Example 3 | PDO | 30 | Conform |
| Example 4/Comparative Example 4 | PGCL | 01 | Conform |
| Example 5/Comparative Example 5 | PGCL | 30 | Conform |

Sample Preparation

The end of the yarn represented in the above Table 4 as the body of the medical thread was heated to prepare the medical thread of Example having a stopper with equilateral triangular cross section (cooling air amount condition: 0.5 mpa).

The length of one side of the equilateral triangular cross section of the stopper in Examples 1, 2 and 4 was 3 mm, and the length of one side of the equilateral triangular cross section of the stopper in Examples 3 and 5 was 2 mm.

Also, the end of the yarn represented in the above Table 4 was heated to prepare the medical thread of Comparative Example having a stopper with circular cross section of substantially the same area as the stopper of Example (cooling air amount condition: 0.5 mpa).

The diameter of the circular cross section of the stopper of Comparative Examples 1, 2 and 4 was 2.38 mm, and the diameter of the circular cross section of the stopper of Comparative Examples 3 and 5 was 1.62 mm.

In Example 1, the distances from the center of gravity of the equilateral triangle, which was the cross section of the stopper, to each vertex were 5.7 times to 7 times of the radius of the circular cross section of the end of the body connected to the stopper.

In Example 2, the distances from the center of gravity of the equilateral triangle, which was the cross section of the stopper, to each vertex were 8.6 times to 9.9 times of the radius of the circular cross section of the end of the body connected to the stopper.

In Example 3, the distances from the center of gravity of the equilateral triangle, which was the cross section of the stopper, to each vertex were 9.2 times to 11.6 times of the radius of the circular cross section of the end of the body connected to the stopper.

In Example 4, the distances from the center of gravity of the equilateral triangle, which was the cross section of the stopper, to each vertex were 8.6 times to 7 times of the radius of the circular cross section of the end of the body connected to the stopper.

In Example 5, the distances from the center of gravity of the equilateral triangle, which was the cross section of the stopper, to each vertex were 9.2 times to 11.6 times of the radius of the circular cross section of the end of the body connected to the stopper.

Test Item and Method

For each medical thread of Examples and Comparative Examples, the stopper attachment force and penetration resistance were measured according to the following methods.

(1) Stopper Attachment Force

Figure 1:
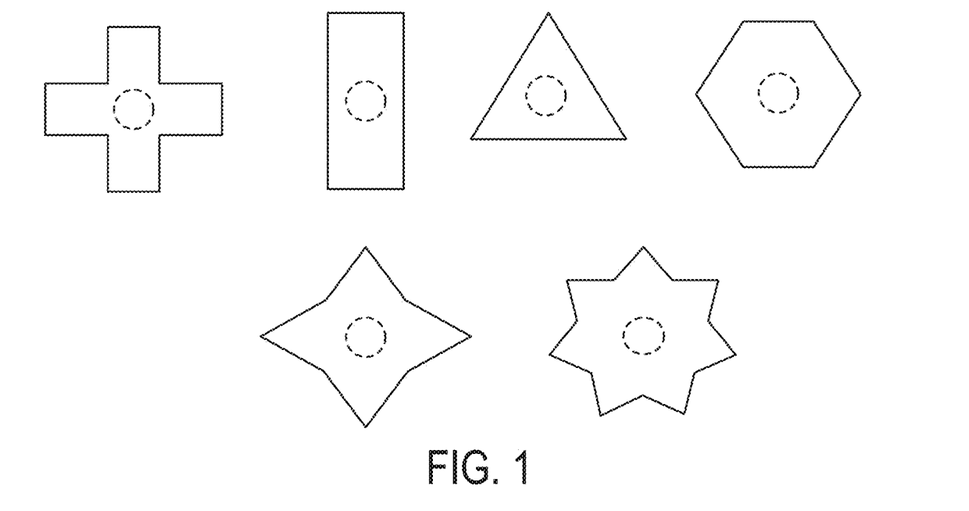
FIG. 1 shows various exemplary cross sections of the stopper that the medical thread according to the present invention can have. (The dotted line in the figure exemplarily represents the circular cross section of the body of the thread.)
Figure 2:
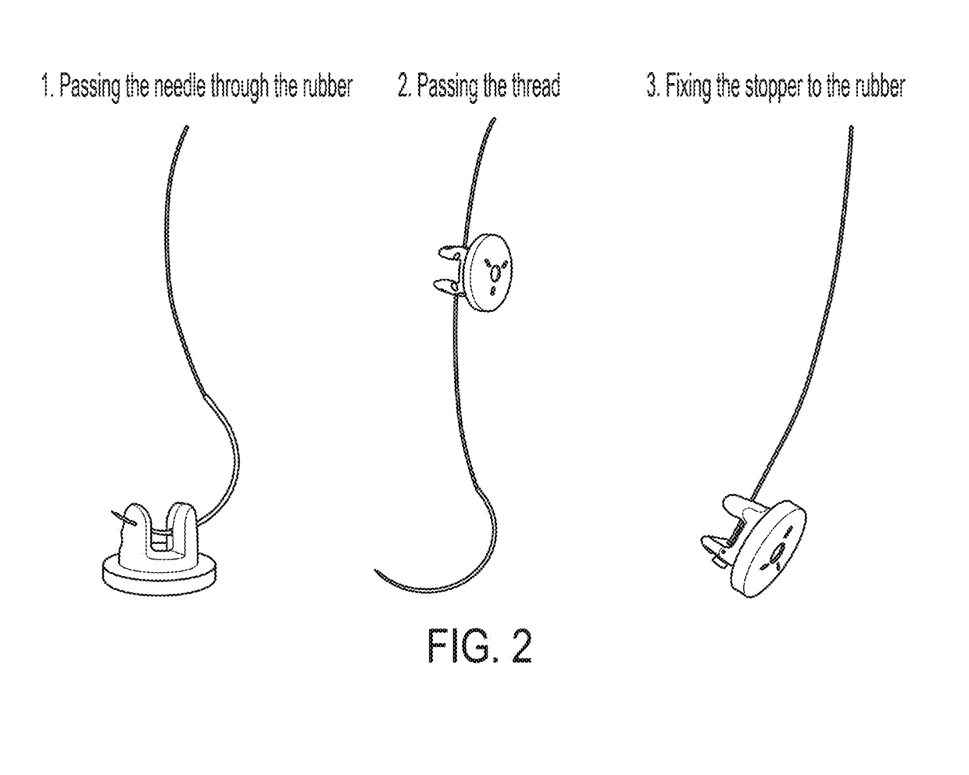
FIG. 2 exemplarily shows a method of fixing a stopper to the rubber for measurement in order to measure the stopper attachment force in the Examples of the present invention.

Test for measuring the force required for the stopper breaking from the body of the medical thread 1) Device Condition for Measurement
Load cell: 50 kgf
Extension range: 200 mm
Speed: 300 mm/min
Length: 130 mm
Number of tests: 6 for each sample 2) Test Method A sample for test was prepared, a needle was passed through the rubber for measuring Tissue Drag, the needle was pulled slowly to fix the stopper to the rubber (FIG. 2), the needle-mounted part was fixed to the upper grip of the tensile strength machine, and the measurement was conducted.

(2) Penetration Resistance

Figure 3:
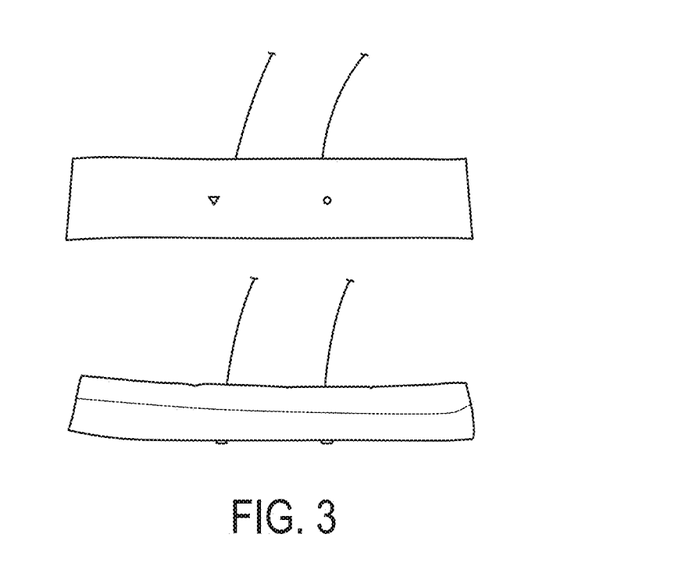
FIG. 3 exemplarily shows a method of fixing a stopper to the skin pad for measurement in order to measure the penetration resistance in the Examples of the present invention.

Test for measuring the strength applied to the stopper during its penetration through skin after fixation to skin pad 1) Device Condition for Measurement
Load cell: 50 kgf
Extension range: 200 mm
Speed: 300 mm/min
Length: 130 mm
Number of tests: 5 for each sample 2) Test Method A sample for test was prepared, the stopper was fixed to skin pad (FIG. 3), the skin pad was fixed to the bottom of the tensile strength machine and the other side was fixed to the upper grip, and the measurement was conducted.

Test Results

1) Stopper Attachment Force (Maximum Load)

|  | No. | Tensile strain at maximum load (%) | Stopper attachment force (kgf) |
|---|---|---|---|
| Example 1 | 1 | 29.50 | 5.13 |
|  | 2 | 30.70 | 5.31 |
|  | 3 | 29.70 | 5.24 |
|  | 4 | 30.00 | 5.55 |
|  | 5 | 29.37 | 5.08 |
|  | 6 | 29.33 | 5.20 |
|  | Average | 29.77 | 5.25 |
|  | Standard deviation | 0.52 | 0.17 |
| Comparative Example 1 | 1 | 28.17 | 4.81 |
|  | 2 | 25.57 | 4.30 |
|  | 3 | 30.13 | 5.43 |
|  | 4 | 24.20 | 4.01 |
|  | 5 | 25.93 | 4.38 |
|  | 6 | 26.83 | 4.76 |
|  | Average | 26.81 | 4.62 |
|  | Standard deviation | 2.10 | 0.50 |
| Example 2 | 1 | 42.30 | 4.69 |
|  | 2 | 42.53 | 4.71 |
|  | 3 | 41.73 | 4.57 |
|  | 4 | 40.53 | 4.35 |
|  | 5 | 40.63 | 4.40 |
|  | 6 | 39.83 | 4.42 |
|  | Average | 41.26 | 4.53 |
|  | Standard deviation | 1.08 | 0.16 |
| Comparative Example 2 | 1 | 34.67 | 3.76 |
|  | 2 | 35.37 | 4.01 |
|  | 3 | 40.27 | 4.40 |
|  | 4 | 36.67 | 3.93 |
|  | 5 | 38.30 | 4.17 |
|  | 6 | 36.50 | 3.78 |
|  | Average | 36.96 | 4.01 |
|  | Standard deviation | 2.04 | 0.24 |
| Example 3 | 1 | 51.83 | 2.67 |
|  | 2 | 53.37 | 2.74 |
|  | 3 | 45.77 | 2.32 |
|  | 4 | 55.97 | 2.87 |
|  | 5 | 47.00 | 2.41 |
|  | 6 | 46.73 | 2.36 |
|  | Average | 50.11 | 2.56 |
|  | Standard deviation | 4.19 | 0.23 |
| Comparative Example 3 | 1 | 35.97 | 1.80 |
|  | 2 | 37.97 | 1.84 |
|  | 3 | 37.00 | 1.82 |
|  | 4 | 37.07 | 1.80 |
|  | 5 | 34.17 | 1.69 |
|  | 6 | 37.87 | 1.80 |
|  | Average | 36.67 | 1.79 |
|  | Standard deviation | 1.42 | 0.05 |
| Example 4 | 1 | 36.17 | 5.33 |
|  | 2 | 38.40 | 5.49 |
|  | 3 | 37.07 | 5.23 |
|  | 4 | 39.10 | 5.36 |
|  | 5 | 37.03 | 5.10 |
|  | 6 | 40.47 | 6.02 |
|  | Average | 38.04 | 5.42 |
|  | Standard deviation | 1.59 | 0.32 |
| Comparative Example 4 | 1 | 38.13 | 5.49 |
|  | 2 | 35.57 | 5.02 |
|  | 3 | 34.97 | 4.88 |
|  | 4 | 36.57 | 5.19 |
|  | 5 | 36.30 | 5.12 |
|  | 6 | 35.93 | 5.19 |
|  | Average | 36.24 | 5.15 |
|  | Standard deviation | 1.08 | 0.20 |
| Example 5 | 1 | 42.40 | 2.84 |
|  | 2 | 43.90 | 2.94 |
|  | 3 | 44.67 | 3.09 |
|  | 4 | 41.07 | 2.62 |
|  | 5 | 40.23 | 2.41 |
|  | 6 | 47.20 | 3.19 |
|  | Average | 43.24 | 2.85 |
|  | Standard deviation | 2.55 | 0.29 |
| Comparative Example 5 | 1 | 41.47 | 2.63 |
|  | 2 | 40.20 | 2.35 |
|  | 3 | 39.80 | 2.52 |
|  | 4 | 43.03 | 2.68 |
|  | 5 | 40.90 | 2.57 |
|  | 6 | 42.17 | 2.60 |
|  | Average | 41.26 | 2.56 |
|  | Standard deviation | 1.22 | 0.12 |

2) Penetration Resistance (Maximum Load)

|  | No. | Tensile strain at maximum Load (%) | Penetration resistance (kgf) |
|---|---|---|---|
| Example 1 | 1 | 24.00 | 0.47 |
|  | 2 | 22.63 | 0.50 |
|  | 3 | 25.23 | 0.42 |
|  | 4 | 22.13 | 0.42 |
|  | 5 | 20.83 | 0.35 |
|  | Average | 22.97 | 0.43 |
|  | Standard deviation | 1.70 | 0.06 |
| Comparative Example 1 | 1 | 20.70 | 0.22 |
|  | 2 | 19.63 | 0.17 |
|  | 3 | 21.47 | 0.24 |
|  | 4 | 18.63 | 0.20 |
|  | 5 | 21.17 | 0.25 |
|  | Average | 20.32 | 0.22 |
|  | Standard deviation | 1.17 | 0.03 |
| Example 2 | 1 | 26.07 | 0.45 |
|  | 2 | 25.17 | 0.46 |
|  | 3 | 26.63 | 0.41 |
|  | 4 | 25.87 | 0.42 |
|  | 5 | 25.00 | 0.40 |
|  | Average | 25.75 | 0.43 |
|  | Standard deviation | 0.67 | 0.03 |
| Comparative Example 2 | 1 | 23.03 | 0.34 |
|  | 2 | 23.73 | 0.40 |
|  | 3 | 22.63 | 0.32 |
|  | 4 | 23.33 | 0.31 |
|  | 5 | 21.17 | 0.34 |
|  | Average | 22.78 | 0.34 |
|  | Standard deviation | 0.99 | 0.03 |
| Example 3 | 1 | 23.63 | 0.21 |
|  | 2 | 25.20 | 0.25 |
|  | 3 | 22.50 | 0.20 |
|  | 4 | 23.70 | 0.22 |
|  | 5 | 23.83 | 0.22 |
|  | Average | 23.77 | 0.22 |
|  | Standard deviation | 0.96 | 0.02 |
| Comparative Example 3 | 1 | 22.27 | 0.15 |
|  | 2 | 22.43 | 0.16 |
|  | 3 | 19.67 | 0.13 |
|  | 4 | 22.47 | 0.17 |
|  | 5 | 18.50 | 0.13 |
|  | Average | 21.07 | 0.15 |
|  | Standard deviation | 1.86 | 0.02 |
| Example 4 | 1 | 25.83 | 0.46 |
|  | 2 | 24.93 | 0.37 |
|  | 3 | 24.53 | 0.42 |
|  | 4 | 24.60 | 0.44 |
|  | 5 | 25.83 | 0.38 |
|  | Average | 25.15 | 0.42 |
|  | Standard deviation | 0.64 | 0.04 |

-continued

| No. | | Tensile strain at maximum Load (%) | Penetration resistance (kgf) |
|---|---|---|---|
| Comparative Example 4 | 1 | 19.97 | 0.20 |
| | 2 | 21.50 | 0.20 |
| | 3 | 20.30 | 0.25 |
| | 4 | 20.40 | 0.21 |
| | 5 | 20.80 | 0.14 |
| | Average | 20.59 | 0.20 |
| | Standard deviation | 0.59 | 0.04 |
| Example 5 | 1 | 27.67 | 0.20 |
| | 2 | 28.70 | 0.26 |
| | 3 | 28.63 | 0.22 |
| | 4 | 25.23 | 0.17 |
| | 5 | 26.37 | 0.22 |
| | Average | 27.32 | 0.21 |
| | Standard deviation | 1.50 | 0.03 |
| Comparative Example 5 | 1 | 24.93 | 0.14 |
| | 2 | 22.67 | 0.13 |
| | 3 | 23.30 | 0.11 |
| | 4 | 25.43 | 0.14 |
| | 5 | 23.27 | 0.13 |
| | Average | 23.92 | 0.13 |
| | Standard deviation | 1.19 | 0.01 |

As can be seen from the above test results, the medical thread according to the present invention exhibits remarkably excellent stopper attachment force and penetration resistance as compared with a thread having a circular stopper of the same area of cross section, and thus by using it, the end can be fixed more firmly to the skin tissue.

The invention claimed is:

1. A medical thread comprising: a body; and a stopper connected to one end of the body,
    wherein the end of the body connected to the stopper has a circular cross section,
    wherein the body is extended along the longitudinal direction,
    wherein the stopper has a polygonal cross section at the part connected to the body,
    wherein three or more of the distances from the center of gravity of the polygonal cross section of the stopper to each vertex of the stopper are 2 times to 15 times the radius of the circular cross section of the end of the body, and
    wherein the penetration resistance of the stopper is 0.2 kgf or higher.

2. The medical thread of claim 1, wherein the stopper is placed perpendicularly to the longitudinal direction of the body adjacent thereto, and has a shape of polygonal prism or polygonal pyramid.

3. The medical thread of claim 1, wherein the stopper has a thickness of 0.1 mm to 5 mm.

4. The medical thread of claim 1, wherein a side of the polygonal cross section of the stopper at the part connected to the body has a length of 1 mm to 5 mm.

5. The medical thread of claim 1, wherein the edge of the stopper is formed in a tapered shape.

6. The medical thread of claim 1, wherein the attachment force between the body and the stopper (stopper attachment force) is 2 kgf or higher.

7. The medical thread of claim 1, wherein each of the body and the stopper independently comprises one or more polymers selected from polydioxanone (PDO), polycaprolactone (PCL), polylactic acid (PLA), polyglycolic acid (PGA), polytrimethylcarbonate (PTMC), polypropylene (PP), Nylon and polytetrafluoroethylene (PTFE), and copolymers thereof.

8. The medical thread of claim 1, wherein the medical thread has a surgical needle combined to the other end of the body which is not the end connected to the stopper.

9. The medical thread of claim 1, wherein the surface of the body comprises plural barbs protruding outward.

10. A method for manufacturing a medical thread, comprising the steps of:
    preparing a body extended along the longitudinal direction;
    heating and melting one end of the body; injecting the melted end of the body into a mold having a predetermined shape to form a stopper at the end of the body;
    cooling and separating the body and the stopper from the mold,
    wherein the end of the body connected to the stopper has a circular cross section,
    wherein the stopper has a polygonal cross section at the part connected to the body,
    wherein three or more of the distances from the center of gravity of the polygonal cross section of the stopper to each vertex of the stopper are 2 times to 15 times the radius of the circular cross section of the end of the body, and
    wherein the penetration resistance of the stopper is 0.2 kgf or higher.

11. The method for manufacturing a medical thread of claim 10, further comprising step of adjusting the position of the stopper relative to the melted end of the body.

12. The method for manufacturing a medical thread of claim 10, wherein, in the step of cooling and separating the body and the stopper from the mold, the body and the stopper are cooled with a cooling air amount of 0.01 to 3 mpa for a time of 5 to 120 seconds.

13. The method for manufacturing a medical thread of claim 10, wherein, in the step of heating and melting one end of the body, the heating temperature is 50 to 400° C.

* * * * *